(12) United States Patent
Kwoen et al.

(10) Patent No.: US 8,841,343 B2
(45) Date of Patent: Sep. 23, 2014

(54) COMPOSITION FOR REPELLING MOSQUITOES

(75) Inventors: Hyouk Il Kwoen, Seoul (KR); Kye Chung Park, Seoul (KR); Hyun Woo Oh, Daejeon (KR)

(73) Assignee: Bio & Hnt, Inc., Seoul (KR)

( * ) Notice: Subject to any disclaimer, the term of this patent is extended or adjusted under 35 U.S.C. 154(b) by 1195 days.

(21) Appl. No.: 11/781,511

(22) Filed: Jul. 23, 2007

(65) Prior Publication Data

US 2008/0161397 A1    Jul. 3, 2008

(30) Foreign Application Priority Data

Dec. 28, 2006 (KR) .................. 10-2006-0136741
Jul. 2, 2007 (KR) .................. 10-2007-0066097

(51) Int. Cl.
*A01N 37/06* (2006.01)

(52) U.S. Cl.
CPC .................................... *A01N 37/06* (2013.01)
USPC ........................................................ 514/557

(58) Field of Classification Search
CPC ........................................................ A01N 37/06
USPC .......................................... 514/557; 424/401
See application file for complete search history.

(56) References Cited

U.S. PATENT DOCUMENTS

| | | | |
|---|---|---|---|
| 3,826,842 A * | 7/1974 | Bordenca et al. | 514/667 |
| 5,175,190 A * | 12/1992 | Burton et al. | 514/560 |
| 6,811,789 B2 | 11/2004 | Sakurai | |
| 2003/0138470 A1 * | 7/2003 | Sakurai et al. | 424/405 |
| 2005/0100563 A1 * | 5/2005 | Hexamer | 424/400 |

FOREIGN PATENT DOCUMENTS

WO    WO2005077175    8/2005

OTHER PUBLICATIONS dictionary definition for the term "solution" (Material Safety data Sheets HyperGlossary, accessed via http://www.ilpi.com/msds/ref/solution.html Apr. 6, 2010.*
Citral MSDS (Sigma-Aldrich revised Feb. 28, 2010, accessed via sigma-aldrich.com Apr. 6, 2010).*
Decanoic acid MSDS (Sigma-Aldrich revised Feb. 26, 2010, accessed via sigma-aldrich.com Apr. 6, 2010).*
Linalool MSDS (Sigma-Aldrich revised Mar. 1, 2010, accessed via sigma-aldrich.com Apr. 6, 2010).*
Geraniol MSDS (Sigma-Aldrich, revised Feb. 27, 2010, accessed via sigma-aldrich.com Apr. 6, 2010).*
Dipropylene glycol MSDS (Sigma-Aldrich, revised Dec. 11, 2008, accessed via sigma-aldrich.com Apr. 6, 2010).*
Geranic acid MSDS (Sigma-Aldrich, revised Aug. 20, 2009, accessed via sigma-aldrich.com Apr. 6, 2010).*
L-citronellol MSDS (Sigma-Aldrich, revised Mar. 31, 2009, accessed via sigma-aldrich.com Apr. 6, 2010).*
Isomenthone MSDS (Lluch Essence, revised Jul. 11, 2007, accessed via www.lluche.com Apr. 6, 2010).*
Jacobson, M. "Chemical Insect Attractants and Repellents" Annu. Rev. Entomol. 1966, 403-422.*
Alexandra Connelly Frost, PhD, "Oil of Lemon Eucalyptus as an Insect Repellent," Aug. 2005, pp. 1-4, http://www.ahcpub.com/hot_topics/?htid=1&httid=1342, AHC Media LLC, Aug. 2005 Hot Topics, Hot Topics Archive.
Wesley G. Taylor and Carl E Schreck, "Chiral-Phase Capillary Gas Chromatography and Mosquito Repellent Activity of Some Oxazolidine Derivatives of (+)- and (−)- Citronellol," Journal of Pharmaceutical Sciences, May 1985, pp. 534-539, vol. 74, No. 5, 1985, American Pharmaceutical Association, Abstract only considered.

* cited by examiner

*Primary Examiner* — Kortney L Klinkel
(74) *Attorney, Agent, or Firm* — Joseph R. Englander; Shutts & BowENLLP

(57) ABSTRACT

The present invention relates to a mosquito repellent comprises at least one or more mosquito repelling compound selected from the group consisting of citronellic acid, geranic acid and derivatives thereof in an effective amount to repel mosquitoes.

17 Claims, No Drawings

COMPOSITION FOR REPELLING MOSQUITOES

TECHNICAL FIELD

The present invention relates to a mosquito repellent, and more particularly, to a new mosquito repellent composition comprising at least one compound selected from the group consisting of citronellic acid, geranic acid and derivatives thereof, which represent excellent mosquito repellent activity, as an independent mosquito repellent compound.

BACKGROUND ART

Some insects are virulent and can cause harm, such as skin irritation, infection, and even disease, to people. In order to protect ourselves from such insects, various types of products have been developed. These products are developed to kill, suppress reproduction or proliferation, and debilitate sensory organs to maim perception.

Among these developed products, debilitation of sensory organs is used for a "repellent." In particular, the repellent is often used for protecting ourselves from mosquitoes. Such a mosquito repellent can paralyze sensory organs of a mosquito and prevent the mosquito from tracing carbon dioxide or odors generated from the skin of a mammal, such as human beings.

Mosquito is a very harmful insect in view of hygiene since it can carry dangerous pathogens for causing disease such as dengue, yellow fever, encephalitis, and malaria. Considering that millions of people die worldwide every year from malaria, it is difficult to ignore the fact that mosquito is a deadly, harmful insect. It is reported that malaria has resurfaced. The number of malaria cases and areas of malaria occurrences have rapidly increased in recent years. Likewise, the number of malaria infected patients has recently increased to reach several thousand patients every year in Korea alone. Notably, the infection rate of malaria has increased every year and as can be inferred from the discussion above, direct or indirect contact with mosquitoes can have potentially dangerous consequence.

To combat mosquitoes, a mosquito repellent is preferably used because it is relatively free from harm to a human body, compared to other mosquito-control methods that mostly use toxic pesticides. At present, various mosquito repellents are available for public. In particular, N,N-diethyl-m-toluamide (DEET) has been the most widely used owing to its excellent mosquito repellent effect. However, since the DEET has an unpleasant odor and strong penetration into the skin, which would be potentially harmful to human, the use of DEET has been restricted from application on children, pregnant women, nursing mothers, hypotensive patients, people with sensitive skin, and so on. Currently, the United States restricts mosquito repellents containing more than 20% DEET from being manufactured for public use.

In view of this, many efforts have been made to replace DEET. Although it is known that citronella, linalool, and lemongrass have repellent activities against mosquitoes, they are less effective than DEET. Due to the low repellent activities, practical use of these materials such as citronella, linalool, and lemongrass for repelling mosquitoes has been restricted.

U.S. Pat. No. 6,811,789 discloses a fragrant composition having a mosquito-repelling effect, which comprises a mixture made of isomenthone, linalool, geraniol, cirtal and citronellol as effective ingredients, wherein the mixture further comprises a fatty acid having 8 to 10 carbon atoms. This composition must contain multiple compounds as an effective mosquito-repelling ingredient and the composition represents repelling effect just equal to the effect of DEET.

Accordingly, tremendous efforts have been made to develop new mosquito repellents derived from natural resources, having more excellent repelling effect than DEET.

DETAILED DESCRIPTION OF THE INVENTION

Technical Problems

A major objective of the present invention is to provide a mosquito repellent composition having excellent mosquito repellent effect.

Another objective of the present invention is to provide a mosquito repellent composition derived from natural resources being harmless to a human body.

Above and other objectives of the present invention could be achieved by the present invention which will be described below.

Technical Solutions

A mosquito repellent composition according to the present invention includes at least one compound selected from the group consisting of citronellic acid, geranic acid and derivatives thereof as an independent mosquito repellent compound.

The mosquito repellent compound is used in the range of 1 to 50 wt % with respect to the total amount of composition.

The present invention includes a method of repelling mosquito, which comprises applying the mosquito repellent composition to the skin.

The present invention also includes a method of repelling mosquito, which comprises the steps of mixing a composition with a liquid solution, wherein the composition comprises at least one mosquito repellent compound selected from the group consisting of citronellic acid, geranic acid and derivatives thereof in an effective amount to repel mosquitoes, and applying the mixed liquid solution to a skin.

Hereinafter, the present invention will be described in detail.

Best Mode for Carrying Out the Invention

In the present invention, it has been confirmed whether various plant materials that can be obtained from nature have mosquito repellent effect. As a result, it has been found that one or more chemical compounds selected from the group consisting of citronellic acid, geranic acid, and derivatives thereof have repellency against mosquito.

The one or more compounds selected from the group consisting of citronellic acid, geranic acid, and derivatives thereof are harmless to a human body and have high repellent activity against mosquitoes.

Citronellic acid and geranic acid have a similar chemical structure and exist in a certain amount in various essential oils such as lemongrass oil and so on. These two compounds have been known as food additives and perfume.

Citronellic acid, which is used in the present invention, can be expressed as a molecular formula, i.e., $C_{10}H_{18}O_2$, and can have a following Chemical Structure 1.

[Chemical Structure 1]

Other names of citronellic acid include (+/−)-citronellic acid; and 3,7-dimethyl-6-octanoic acid.

Citronellic acid can be known as a natural compound which exists in a plant like lemon tree and can be used as food additives.

Geranic acid, which is used in the present invention, can be expressed as a molecular formula, i.e., $C_{10}H_{16}O_2$, and has a following Chemical Structure 2.

[Chemical Structure 2]

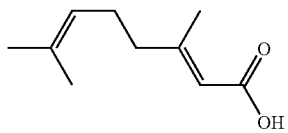

Geranic acid is known to exist as a natural plant compound in tea trees, tomatoes, wine or the like. Furthermore, it has been used as food additives and used for preparing perfume.

The chemical structures of the aforementioned citronellic acid and geranic acid can be modified to manufacture a derivative for a new repellent which may represent high repellent activity to mosquitoes.

In the present invention, compounds used as the aforementioned mosquito repellent can be used alone or mixed with a well-known solvent to manufacture a mosquito repellent composition. The well-known solvent includes either a solvent used for a general repellent composition or a doping material applied to the skin of a human body, having a type of a cream, a liquid phase, a spray, and a gel. In this case, the citronellic acid, geranic acid and derivatives thereof are used alone or in combination. In this case, citronellic acid, geranic acid and derivatives thereof are used in the range of 1 to 50 wt % with respect to a weight of the total amount of mosquito repellent composition. If used less than 1 wt %, repellent activity may be insufficient.

The mosquito repellent composition according to the present invention is preferably used in such a manner that it is applied to the skin in a type of a cream, a lotion, a spray, a spreader, or an ointment. The mosquito repellent composition is used in a place where mosquitoes inhabit. The expression, "applied to the skin" includes "applied to a path of a mosquito for contact to the skin, such as clothes and door," as well as "directly applied to the skin." Furthermore, it is expected that the mosquito repellent composition can be used as a repellent for arthropod of various species in addition to mosquitoes.

The present invention will be embodied by the following embodiment, and the following embodiment is only a detailed exemplary of the present invention and is not intended to restrict or limit the protection scope of the present invention.

MODE FOR CARRYING OUT THE INVENTION

Embodiment

Preparation of Sample

Citronellic acid and geranic acid, which are used in the present invention, are commercially available or can directly be synthesized. In this embodiment, products of Aldrich Co. (product names are respectively Citronellic acid and Geranic acid) were purchased and used as citronellic acid and geranic acid. Purities of the above two compounds were examined using a gas chromatograph (GC) and a gas chromatograph-mass spectrometry (GC-MS). The compounds having purity of 99.5% or greater were only used. Respective ingredients of the above compounds were added to isopropyl alcohol of 91% to make test samples consisting of a solution in the concentration of 0.5 to 50%. The samples were used for mosquito repellent efficacy experiments.

The test samples manufactured as above underwent repellent effective experiments with respect to *Aedes* which is a main mosquito group attacking human.

Examination Test Mosquitoes Used in the Experiments

In this embodiment, *Aedes aegypti* was used as test mosquitoes. The *Aedes aegypti* was supplied from Korea Research Institute of Bioscience and Biotechnology and reared indoor from generation to generation.

The larvae of the *Aedes aegypti* were reared in a plastic container of 22×14×7 cm containing distilled water with small amount of one-to-one mixture of chicken feed and yeast. Fresh mosquito pupae were transferred into a paper cup containing water and then placed in a transparent rearing cage to emerge as adults. Here, the rearing cage was constructed with metal net. Males and females of the freshly emerged mosquitoes were transferred to a rearing cage at one-to-one ratio, and left for two or three days for mating. The female mosquitoes were then used for repellency tests. Eight percent (8%) sugar water was supplied for the adult mosquitoes. The following rearing conditions were maintained: light condition of 16 h:8 h (day:night), temperature of 27±2° C., and relative humidity of 80±10%.

Examination of Repellent Activity Using Skin Test

In order to examine effectiveness of the mosquito repellent of the prepared sample solutions, one (1) ml of a sample solution was uniformly applied, using a metal rod, on a forearm of a volunteer human test subject between wrist and elbow. Thereafter, the arm treated with the test solution was inserted in a bioassay cage, constructed with Plexiglass of 50×50×50 cm containing approximately 100 mated female mosquitoes. The number of mosquitoes trying to bite was recorded for three minutes in every thirty minutes for up to 4 hours or in every hour for up to 12 hours. The time required to get the arm bitten by two cumulative mosquitoes was regarded as effective repellency duration. A net window of 40×40 cm was present at each side and top of the Plexiglass bioassay cage to allow air ventilation. A 15×15 cm hole was prepared at the front side of the Plexiglass bioassay cage and a long net sleeve was attached to the hole so that the test arm could be put into the cage for repellency test.

At the beginning of each repellency test, an arm treated with no solvent was placed in the bioassay cage containing mosquitoes, in order to examine blood feeding activity of the mated female test mosquitoes. The repellency tests with the test solutions were carried out only when the arm was bitten by at least two mosquitoes for initial three minutes.

Results of Examination of Repellent Activity of each Ingredient

Repellent activity against *Aedes* was examined in accordance with the aforementioned method using the samples which respectively contain citronellic acid and geranic acid. Also, mosquito repellent activity was measured with solutions which contain DEET and Picadirin, wherein the DEET and Picadirin are commercially available mosquito repellents which are currently recommended by the Center for Disease Control of the United States. The test results were shown in Table 1 to Table 6.

TABLE 1

| Compound | Concentration | Effective repellency duration (minute) (mean ± standard deviation) |
|---|---|---|
| Citronellic acid | 0.5% | 0 ± 0 |
| Geranic acid | 0.5% | 0 ± 0 |
| Citronellic acid | 2% | 60 ± 0 |

TABLE 1-continued

| Compound | Concentration | Effective repellency duration (minute) (mean ± standard deviation) |
|---|---|---|
| Geranic acid | 2% | 195 ± 45.0 |
| DEET | 2% | 70 ± 10.0 |

Table 1 indicates effective repellency duration of each compound at the concentration of 0.5% and 2%, represented as protection time until the arm was bitten by two cumulative mosquitoes. In this case, the dose amount of the concentration of 0.5% corresponds to 0.0125 mg/cm$^3$ and 2% to 0.05 mg/cm$^3$.

TABLE 2

| Compound | Concentration | Effective repellency duration (minute) (mean ± standard deviation) |
|---|---|---|
| Citronellic acid | 10% | 240 ± 0 |
| Geranic acid | 10% | 240 ± 0 |
| DEET | 10% | 218 ± 10.8 |
| Picadrin | 10% | 158 ± 27.5 |

Table 2 indicates effective repellency duration of each compound at the concentration of 10%, represented as protection time until the arm was bitten by two cumulative mosquitoes. In this case, the dose amount of the concentration of 10% corresponds to 0.25 mg/cm$^3$, and the maximum measurement time was 240 minutes.

As shown in Table 1 and Table 2 above, effective repellency durations of both citronellic acid and geranic acid lasted for 240 minutes at the level of 0.25 mg/cm$^3$. It is noted that citronellic acid and geranic acid have greater mosquito repellent effect than that of DEET or Picadrin. The effective repellency duration of DEET lasted for 218 minutes and the effective repellency duration of Picadirin lasted for 158 minutes. At the level of 0.05 mg/cm$^3$, geranic acid lasted for 195 minutes while DEET lasted for 70 minutes. However, citronellic acid and geranic acid did not represent any repellency at the level of 0.0125 mg/cm$^3$.

TABLE 3

| Compound | Concentration | Effective repellency duration (hour) (mean ± standard deviation) |
|---|---|---|
| Citronellic acid | 15% | 5.7 ± 2.03 |
|  | 30% | 9.3 ± 1.76 |
|  | 50% | 9.3 ± 1.76 |
| Geranic acid | 15% | 6.7 ± 1.20 |
|  | 30% | 10.0 ± 2.00 |
|  | 50% | 12.0 ± 0 |

Table 3 indicates effective repellency duration of each compound at the concentration of 15%, 30% and 50% respectively, represented as protection time until the arm was bitten by two cumulative mosquitoes. In this case, the dose amount of the concentration of 15% corresponds to 0.375 mg/cm$^3$, 30% to 0.75 mg/cm$^3$ and 50% to 1.25 mg/cm$^3$. The maximum measurement time was 12 hours.

As shown in Table 3 above, effective repellency duration of citronellic acid and geranic acid increased with the higher dose amount. Effective repellency duration of citronellic acid lasted 9.3 hours at the dose amount of 0.75 to 1.25 mg/cm$^3$, and geranic acid lasted 10 hours at the dose amount of 0.75 mg/cm$^3$ and 12 hours at 1.25 mg/cm$^3$.

TABLE 4

| Compound | Concentration | Repellent efficiency (%) per time (minutes) | | | | | | | |
|---|---|---|---|---|---|---|---|---|---|
|  |  | 30 | 60 | 90 | 120 | 150 | 180 | 210 | 240 |
| Citronellic acid | 2% | 100 | 84.7 | 71.3 | 56.4 | 37.8 | 15.2 | 7.4 | 0 |
| Geranic acid | 2% | 100 | 100 | 100 | 100 | 83.3 | 50.0 | 50.0 | 33.3 |
| DEET | 2% | 100 | 0 | 0 | 0 | 0 | 0 | 0 | 0 |

Table 4 indicates a repellent efficiency measured every 30 minutes after test solution was applied on an arm at the concentration of 2%. In this case, the dose amount of the concentration of 2% corresponds to 0.05 mg/cm$^3$.

TABLE 5

| Compound | Concentration | Repellent efficiency (%) per time (minutes) | | | | | | | |
|---|---|---|---|---|---|---|---|---|---|
|  |  | 30 | 60 | 90 | 120 | 150 | 180 | 210 | 240 |
| Citronellic acid | 10% | 100 | 100 | 100 | 100 | 100 | 85.7 | 71.4 | 57.1 |
| Geranic acid | 10% | 100 | 100 | 100 | 100 | 100 | 100 | 100 | 87.5 |
| DEET | 10% | 100 | 100 | 100 | 100 | 87.5 | 81.3 | 78.1 | 71.9 |
| Picadirin | 10% | 85.0 | 85.0 | 85.0 | 80.0 | 75.0 | 72.5 | 62.5 | 47.5 |

Table 5 indicates a repellent efficiency measured every 30 minutes after test solution was applied on an arm at the concentration of 10%. In this case, the dose amount of the concentration of 10% corresponds to 0.25 mg/cm$^3$.

The results of Table 4 and Table 5 above indicate that citronellic acid showed strong repellent efficiency of 100% for 30 minutes and geranic acid for 120 minutes at the level of 0.05 mg/cm$^3$. The citronellic acid and geranic acid showed greater repellent activity than that of DEET at the same level and even after 30 and 120 minutes respectively. Further, citronellic acid indicated strong repellent efficiency of 100% for 150 minutes and geranic acid for 210 minutes at the level of 0.25 mg/cm³. The citronellic acid and geranic acid showed even greater repellent activity than that of DEET whose repel-tection time until the arm was bitten by two cumulative mosquitoes. In this case, the dose amount of the concentration of lent efficiency of 100% for 120 minutes at the same level or that of picadirin for less than 30 minutes.

TABLE 6

| Compound | Concentration | Repellent efficiency (%) per time (hours) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Citronellic acid | 15% | 100 | 75 | 75 | 75 | 50 | 50 | 37.5 | 37.5 | 25 | NA | NA | NA |
| | 30% | 100 | 87.5 | 75 | 75 | 75 | 62.5 | 62.5 | 62.5 | 62.5 | 50 | 50 | 50 |
| | 50% | 100 | 100 | 100 | 100 | 93.3 | 86.7 | 86.7 | 86.7 | 80 | 73.3 | 73.3 | 73.3 |
| Geranic acid | 15% | 100 | 100 | 100 | 81.8 | 72.7 | 54.5 | 54.5 | 54.5 | 45.5 | NA | NA | NA |
| | 30% | 100 | 100 | 100 | 100 | 100 | 85.7 | 85.7 | 85.7 | 85.7 | 85.7 | 78.6 | 71.4 |
| | 50% | 100 | 100 | 100 | 100 | 100 | 100 | 100 | 100 | 100 | 100 | 90 | 80 |

In Table 6, "NA" means that the test was not carried out.

Table 6 indicates repellent efficiency per time of each compound at the concentration of 15%, 30% and 50% respectively. In this case, the dose amount of the concentration of 15% corresponds to 0.375 mg/cm³, 30% to 0.75 mg/cm³ and 50% to 1.25 mg/cm³. The maximum measurement time was 12 hours.

From the Table 6, we could understand that the more dose amount applied, the higher repellent efficiency obtained. Citronellic acid indicated strong repellent efficiency of almost 90% for 8 hours at the level of 1.25 mg/cm³, and geranic acid also indicated strong repellent efficiency of almost 90% for 10 hours at the level of 0.75 mg/cm³, and 100% for 10 hours at the level of 1.25 mg/cm³.

In Table 4 to Table 6, the repellent efficiency was calculated using the following Equation 1.

$$\text{Repellent efficiency}(\%) = \frac{\left(\begin{array}{c}\text{number of mosquitoes of control example} - \\ \text{number of mosquitoes of experiment example}\end{array}\right)}{\text{number of mosquitoes of control example}} \times 100$$

[Equation 1]

From the results of Table 1 to 6 above, it is noted that citronellic acid and geranic acid have greater mosquito repellent effect than that of DEET or Picadirin, which are commercially available mosquito repellents which are currently recommended by the Center for Disease Control of the United States.

It will be apparent to those skilled in the art that the present invention can be embodied in other specific forms without departing from the spirit and essential characteristics of the invention.

What is claimed is:

1. A method of repelling mosquito, which comprises the steps of:
   selecting a composition consisting of geranic acid in isopropyl alcohol, wherein the geranic acid is used as an effective ingredient in an effective amount to repel mosquitoes, wherein the geranic acid concentration in the isopropyl alcohol is between about 0.5 wt % and about 50 wt %; and
   applying the composition to the skin of a subject in need of repelling mosquito.

2. The method as defined in claim 1, wherein the geranic acid has a following Chemical Structure 2:

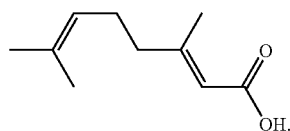

[Chemical Structure 2]

3. The method as defined in claim 1, wherein the geranic acid is used in the range of 1 to 50 wt % with respect to the total amount of composition.

4. The method as defined in claim 1, wherein the geranic acid is used in the range of about 0.5 wt % to about 2 wt % with respect to the total amount of composition.

5. The method as defined in claim 1, wherein the composition is formulated as a lotion, a spray, a spreader, or an ointment.

6. A method of repelling mosquito, which comprises the steps of:
   selecting a composition consisting of geranic acid in isopropyl alcohol, wherein the geranic acid is used as an effective ingredient in an effective amount to repel mosquitoes, wherein the geranic acid concentration in the isopropyl alcohol is about 10 wt % and
   applying the composition to the skin of a subject in need of repelling mosquito.

7. The method as defined in claim 6, wherein the geranic acid has a following Chemical Structure 2:

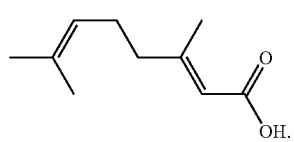

[Chemical Structure 2]

8. The method as defined in claim 6, wherein the composition is formulated as a lotion, a spray, a spreader, or an ointment.

9. A method of repelling mosquito, which comprises the steps of:
   selecting a composition consisting of geranic acid in isopropyl alcohol, wherein the geranic acid is used as an effective ingredient in an effective amount to repel mosquitoes, wherein the geranic acid concentration in the isopropyl alcohol is about 15 wt % and
   applying the composition to the skin of a subject in need of repelling mosquito.

10. The method as defined in claim 9, wherein the geranic acid has a following Chemical Structure 2:

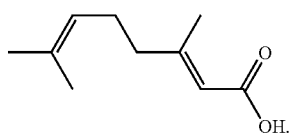

[Chemical Structure 2]

11. The method as defined in claim 9, wherein the composition is formulated as a lotion, a spray, a spreader, or an ointment.

12. A method of repelling mosquito, which comprises the steps of:

selecting a composition consisting of geranic acid in isopropyl alcohol, wherein the geranic acid is used as an effective ingredient in an effective amount to repel mosquitoes, wherein the geranic acid concentration in the isopropyl alcohol is about 30 wt % and applying the composition to the skin of a subject in need of repelling mosquito.

13. The method as defined in claim 12, wherein the geranic acid has a following Chemical Structure 2:

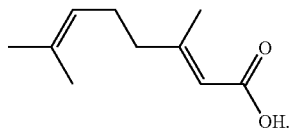

[Chemical Structure 2]

14. The method as defined in claim 12, wherein the composition is formulated as a lotion, a spray, a spreader, or an ointment.

15. A method of repelling mosquito, which comprises the steps of:

selecting a composition consisting of geranic acid in isopropyl alcohol, wherein the geranic acid is used as an effective ingredient in an effective amount to repel mosquitoes, wherein the geranic acid concentration in the isopropyl alcohol is about 50 wt % and applying the composition to the skin of a subject in need of repelling mosquito.

16. The method as defined in claim 15, wherein the geranic acid has a following Chemical Structure 2:

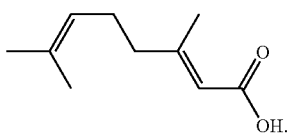

[Chemical Structure 2]

17. The method as defined in claim 15, wherein the composition is formulated as a lotion, a spray, a spreader, or an ointment.

\* \* \* \* \*